(12) United States Patent
Lechot

(10) Patent No.: US 6,669,702 B2
(45) Date of Patent: Dec. 30, 2003

(54) MODULAR TOOL CONNECTION ASSEMBLY

(75) Inventor: André Lechot, Orvin (CH)

(73) Assignee: Precimed S.A., Orvin (SE)

( * ) Notice: Subject to any disclaimer, the term of this patent is extended or adjusted under 35 U.S.C. 154(b) by 160 days.

(21) Appl. No.: 10/073,072

(22) Filed: Feb. 9, 2002

(65) Prior Publication Data

US 2002/0111632 A1 Aug. 15, 2002

Related U.S. Application Data

(60) Provisional application No. 60/267,889, filed on Feb. 10, 2001.

(51) Int. Cl.[7] .................................................. A61B 17/56
(52) U.S. Cl. ........................ 606/86; 408/239; 279/103; 606/1
(58) Field of Search .................... 606/1, 86; 279/102, 279/103; 408/239

(56) References Cited

U.S. PATENT DOCUMENTS

| | | | | |
|---|---|---|---|---|
| 1,243,310 A | * | 10/1917 | Littman | 279/102 |
| 1,340,845 A | * | 5/1920 | Strong | 279/103 |
| 4,834,717 A | * | 5/1989 | Haber et al. | 604/193 |
| 5,062,749 A | * | 11/1991 | Sheets | 279/75 |
| 6,273,882 B1 | * | 8/2001 | Whittier et al. | 606/1 |

* cited by examiner

Primary Examiner—Kevin Shaver
Assistant Examiner—Michael B. Priddy
(74) Attorney, Agent, or Firm—Bugnion S.A.; John Moetteli

(57) ABSTRACT

A modular tool connection assembly includes a housing which defines the main axis of assembly with a linear bore for containing the components of the assembly. The housing contains a connector component presenting a first taper portion. The connector is retained in the linear bore of the housing with a spring interposed between the connector and the housing. A tool containing a second taper portion is placed in axial engagement with the first taper causing the components to be securely connected. The spring limits the force applied between the taper portions allowing them to be disconnected easily.

4 Claims, 3 Drawing Sheets

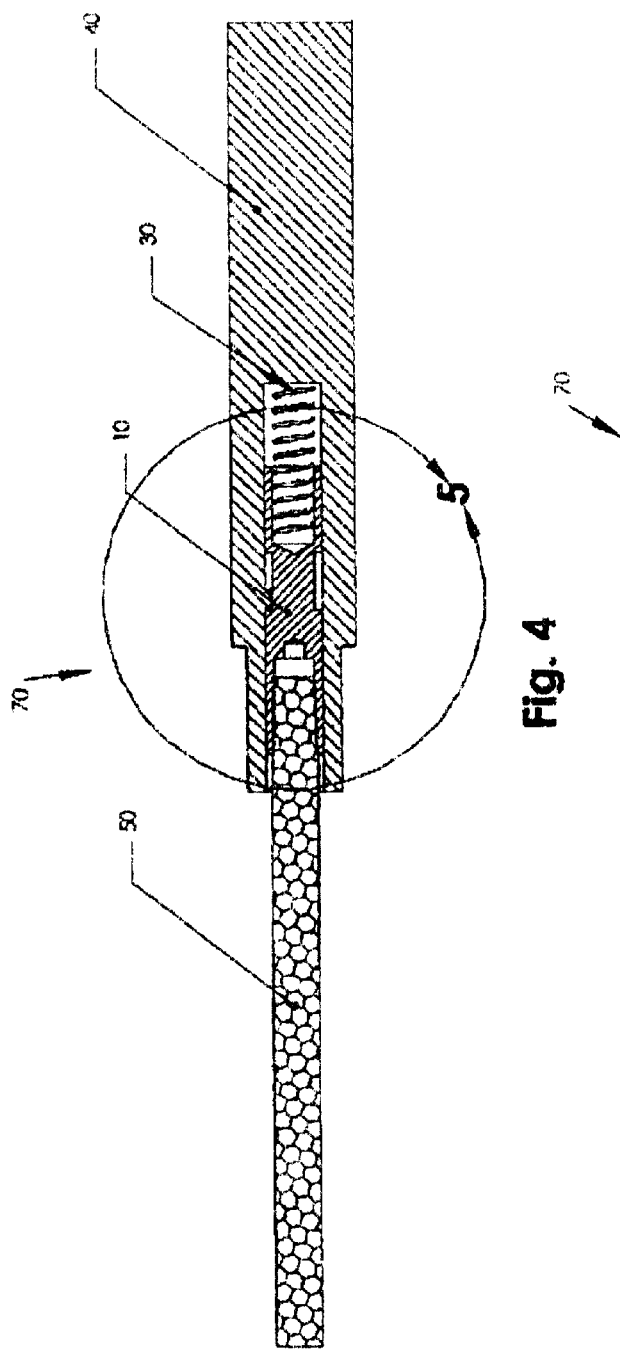
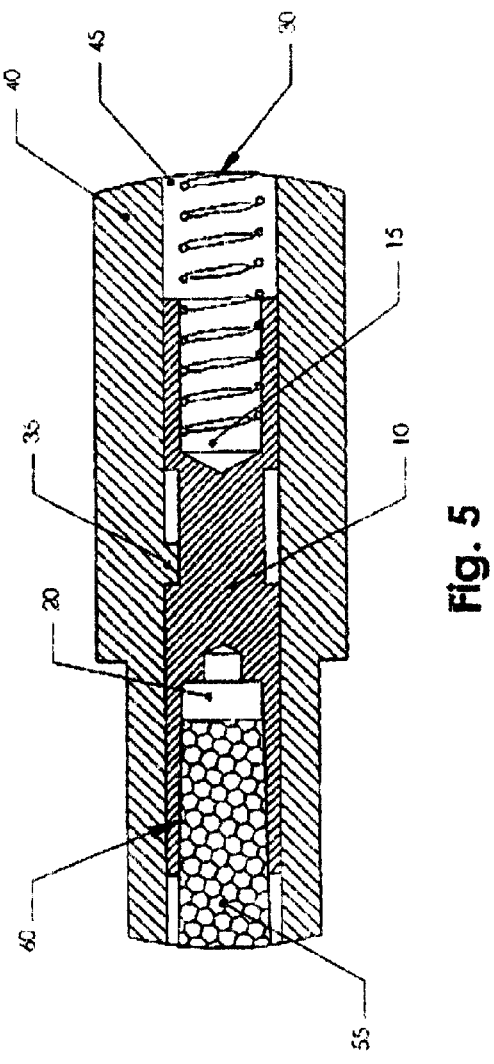
Fig. 4
Fig. 5

MODULAR TOOL CONNECTION ASSEMBLY

This application claims the benefit of Provisional application Ser. No. 60/267,889, filed Feb. 10, 2001.

BACKGROUND OF THE INVENTION

This invention generally relates to modular connections useful in Orthopedic and Industrial tool design to create a quick connect and disconnect function while maintaining a rigid connection. Of particular interest are modular tool junctions wherein the interface gives the user a sensation or feeling similar to a one piece construction. It is necessary, for instance, in some surgical procedures for a surgeon who is using a handled instrument (such as a screw driver, a tap, a reamer, or a countersink) to feel the quality of the bone when he is using the instrument (such as drilling or tapping the bone or screwing something into it). This need for sensation during the surgery has forced some manufactures of surgical products to manufacture a one piece instrument integral with the handle. When sensation is not necessary, companies often provide surgeons with a modular handle with several different tools that interface into it. With the rising costs of healthcare, companies are searching for solutions to reduce their cost for necessary surgical instrumentation while trying not to compromise the surgeon's sensation requirements. To meet this need, one idea was presented using a tool collet that was integrated with a handle. The surgeon places the shaft of a tool into the collet and then activates the collet using a threaded sleeve. The threaded sleeve when turned closes the collet which in turn creates a solid connection to the tool shaft. The collet functions well, however it can be clumsy and rather a slow method of interchanging the tools. These factors create additional surgical time which is unacceptable for containment of cost.

It is the primary aim of the present invention to provide a modular connection for surgical and industrial tool designs which is quick to connect. There is also a need to create a connection that is rigid. There is a further need to create a connection that is reversible. There is still further need for a tool connection that consists of mating tapers. There is yet still a further need for a tool connection with mating tapers whose connection force is limited by a spring.

SUMMARY OF THE INVENTION

To accomplish these objectives, the invention comprises a housing which defines the main axis of assembly with a linear bore for containing the components of the assembly. The housing contains a connector component presenting a first taper portion. The connector is retained in the linear bore of the housing with a spring interposed between the connector and the housing. A tool containing a second taper portion is placed in axial engagement with the first taper causing the components to be securely connected. The spring limits the force applied between the taper portions allowing them to be disconnected easily.

BRIEF DESCRIPTION OF THE DRAWINGS

FIG. 4 shows a cross section of a side view of the assembled modular tool connection assembly embodying the present invention.

FIG. 5 shows a blown up cross section of the side view of the assembled modular tool connection show in FIG. 4.

DETAILED DESCRIPTION OF THE DRAWINGS

Figure 1:
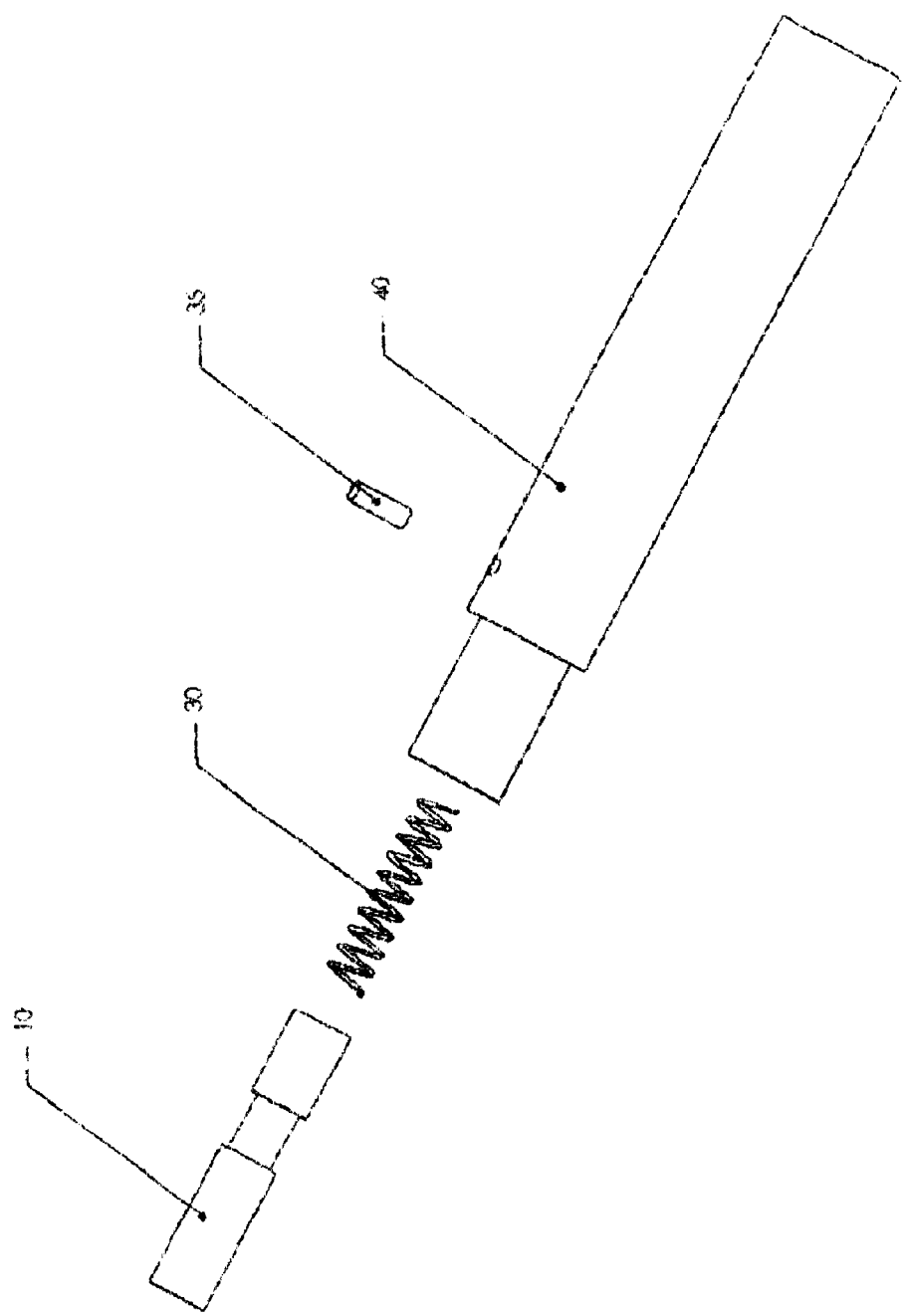
FIG. 1 shows an exploded isometric view of an un-assembled modular tool connection assembly embodying the present invention.
Figure 2:
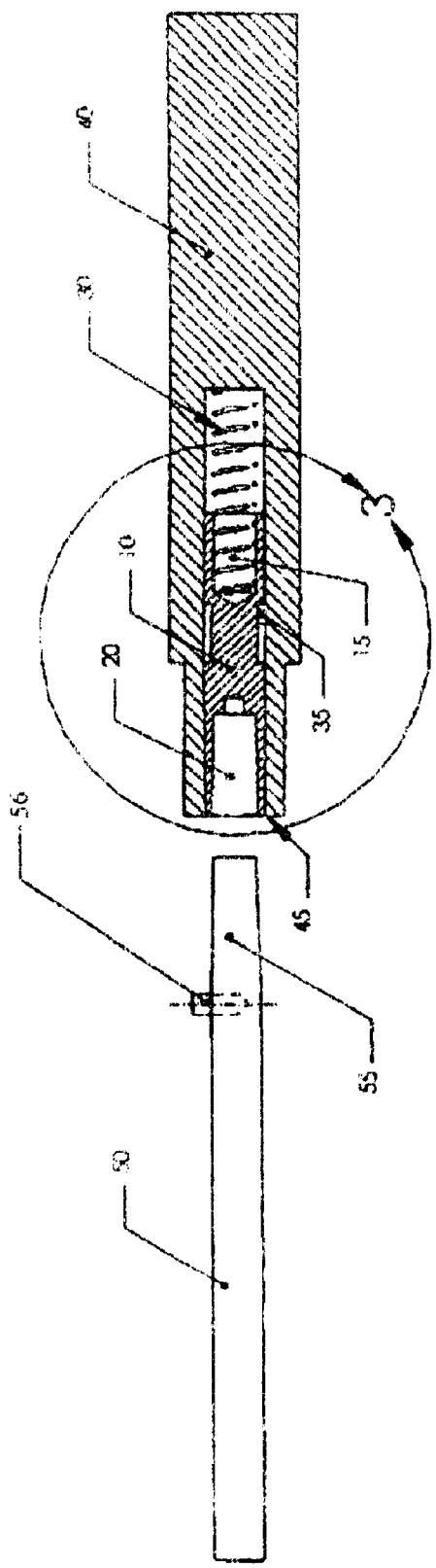
FIG. 2 Shows a cross section of a side view of the un-assembled modular tool connection of FIG. 1.
Figure 3:
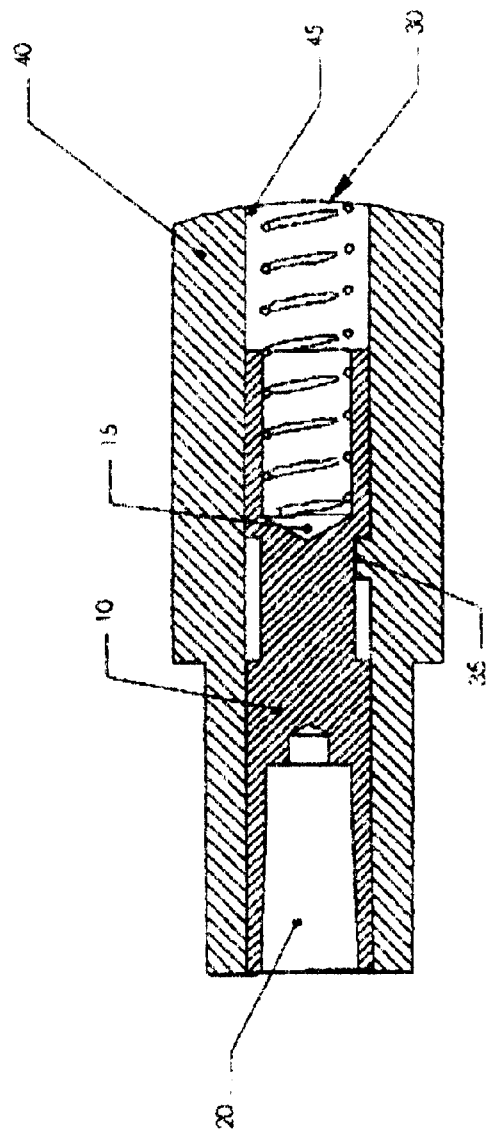
FIG. 3 shows a blown up cross section of the side view of the un-assembled modular tool connection shown in FIG. 2.

One preferred embodiment of the present invention is displayed in FIGS. 1–5. Generally shown in FIG. 1 is an exploded view of the assembly comprising of a connector 10, a spring 30, a housing 40, and a retaining pin 35. These components are shown in a pre-assembled orientation as seen in FIGS. 2–5. The connector 10 is pre-assembled in the bore 45 of the housing 40 and restrained with the retaining pin 35. The spring 30 is also pre-assembled interpositionally therebetween. The spring 30 rests in the bore 45 of the housing 40 and is centered in a second bore 15 which is located in the connector 10. In cross-section, the connector 10 also contains a first taper 20 useful for mating with a second taper 55 on the tool 50. An abuttement 56 prevents the tool 50 from entering into the bore 45 to an extent that the connector component would bottom out against the retainer 35, thus insuring a consistent removal force.

A complete assembly 70 is shown in FIGS. 4–5 wherein the spring 30 is shown in a compressed state and the mating taper junction 60 is shown. The spring 30 acts as a force limiter during the assembly process not allowing the user to place too much force into the mating taper junction 60. Because the assembly force is limited, it is easy to remove the tapers 20, 55 on disassembly simply by pulling them apart. The tapers 20, 55 also act to center the junction 60 and can be in the form of a morse taper which is commonly used for separable junctions. Depending on the application, it may be necessary to apply torque or axial force through this junction 60 which can be achieved by adding additional retention mechanisms which are not shown. For example other medical instrument retention mechanisms such as the small, mini, or large AO connection the Zimmer Hall, or a bayonet system may be combined with the present invention to create an extremely stable modular junction. These retention mechanisms may also hold the spring 30 in a compressed state similar to that shown in FIGS. 4.5 when assembled. This will allow the spring to retain a light force in the taper junction 60 while in the assembled state. This tension can be useful for ensuring that the tapers 20, 55 remain rigid during use of the assembly 70. The housing 40 can also be a part of a handle assembly of a component of another instrument. What is important to the instant inventor is the use of the force limited junction to create stability in a modular instrument construct so that there is no play between the junctions.

Although the invention has been described with reference to preferred embodiments thereof, it is evident to those of skill in the art that various modifications and improvements may be made without departing from the spirit and scope of the invention as defined by the appended claims.

What is claimed:

1. A connecting assembly for surgical use, comprising a housing assembly including a housing, a connector component, and a spring, the housing defining an axial bore for containing the connector component and the spring, the connector component presenting a first taper portion, the connector component being retained in the axial bore of the housing with a spring interposed between the connector component and the housing, and a surgical tool containing a second taper portion, wherein engagement of the tapers in the bore causes the tool and the housing assembly to be securely connected while the spring limits the force applied between the taper portions allowing the assembly to be reversed by pulling the tool from the bore of the housing assembly.

2. The connecting assembly of claim 1, wherein the surgical tool is selected from a group of surgical tools consisting of a screw driver, a tap, a reamer, and a countersink.

3. The connecting assembly of claim 1, wherein a pin retains the connector component, the pin engaging a recess of the connector component.

4. The connecting assembly of claim 1, wherein the surgical tool includes an abuttement which prevents the tool from entering into the bore to an extent that the connector component would bottom out, thus insuring a consistent removal force.

* * * * *

UNITED STATES PATENT AND TRADEMARK OFFICE
CERTIFICATE OF CORRECTION

PATENT NO. : 6,669,702 B2
DATED : December 30, 2003
INVENTOR(S) : Lechot

It is certified that error appears in the above-identified patent and that said Letters Patent is hereby corrected as shown below:

<u>Title page,</u>
Item [73], Assignee, replace "Precined S.A., Orvin (SE)" with -- Precimed S.A., Orvin (CH) --

Signed and Sealed this

Twenty-fourth Day of February, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,669,702 B2  Page 1 of 1
DATED : December 30, 2003
INVENTOR(S) : Lechot It is certified that error appears in the above-identified patent and that said Letters Patent is hereby corrected as shown below:

Title page,
Item [73], Assignee, replace "Precined S.A., Orvin (SE)" with -- Precimed S.A., Orvin (CH) --

Signed and Sealed this

Second Day of March, 2004

JON W. DUDAS
*Acting Director of the United States Patent and Trademark Office*